(12) United States Patent
Lui et al.

(10) Patent No.: US 9,815,766 B2
(45) Date of Patent: Nov. 14, 2017

(54) PROCESS FOR DOUBLE CARBONYLATION OF ALLYL ETHERS TO CORRESPONDING DIESTERS

(71) Applicant: EVONIK DEGUSSA GMBH, Essen (DE)

(72) Inventors: Jie Lui, Zhuzhou (CN); Li Haoquan, Zhongshan (CN); Matthias Beller, Ostseebad Nienhagen (DE); Ralf Jackstell, Cuxhaven Altenwalde (DE); Robert Franke, Marl (DE); Katrin Marie Dyballa, Recklinghausen (DE)

(73) Assignee: EVONIK DEGUSSA GMBH, Essen (DE)

( * ) Notice: Subject to any disclaimer, the term of this patent is extended or adjusted under 35 U.S.C. 154(b) by 0 days.

(21) Appl. No.: 15/378,538

(22) Filed: Dec. 14, 2016

(65) Prior Publication Data
US 2017/0174609 A1    Jun. 22, 2017

(30) Foreign Application Priority Data

Dec. 16, 2015 (EP) .................................. 15200511

(51) Int. Cl.
*C07C 67/36* (2006.01)
*C07C 67/37* (2006.01)

(52) U.S. Cl.
CPC ................... *C07C 67/37* (2013.01)

(58) Field of Classification Search
CPC .................................................. C07C 67/37
See application file for complete search history.

(56) References Cited

U.S. PATENT DOCUMENTS

| 4,622,416 A | 11/1986 | Hanes et al. |
| 5,004,568 A | 4/1991 | Hanes et al. |

OTHER PUBLICATIONS

International Search Report for EP 15 20 0511 dated May 19, 2016 (1 page).
Knifton, John F. Syngas Reactions: II The homogeneous catalyzed carbonylation and cyclization of all allylic substrates. Journal of Organometallic Chemistry, 188, 1980, pp. 223-236.
Liu, Qiang, et at, Domino Catalysis: Palladium-Catalyzed Carbonylation of Allylic Alcohols to β,γ-Unsaturated Esters. Angewandte Chemie International Edition, 2013, 52, pp. 8064-8068.
Werle, et al. Alcohols, Polyhydric, Ullmann's Encyclopedia of Industrial Chemistry. 2002, vol. 2, 265-284.
Tsuji et al. Organic Syntheses by Means of Noble Metal Compounds, VIII. Catalytic Carbonylation of Allylic Compounds with Palladium Chloride. Journal of the American Chemical Society, 1964, 86 (20), 4350-4353.
Liu et al. Ligand-Controlled Palladium-Catalyzed Alkoxycarbonylation of Allenes: Regioselective Synthesis of α,β- and β,γ-Unsaturated Esters. Journal of the American Chemical Society, 2015, 137, 8556-8563.
Reppe et al, Carbonylierung II Carbonsäuren und ihre Derivate aus olefinischen Verbindungen und Kohienoxyd [Carbonylation II. Carboxylic Acids and Their Derivatives from Olefinic Compounds and Carbon Dioxide], Justus Liebigs Annalen der Chemie, 1953, 582, 1, 38-71.

*Primary Examiner* — Yevegeny Valenrod
*Assistant Examiner* — Blaine G Doletski
(74) *Attorney, Agent, or Firm* — Smith, Gambrell & Russell, LLP

(57) ABSTRACT

The invention relates to a process for doubly carbonylating allyl ethers to the corresponding diesters, wherein a linear or branched allyl ether is reacted with a linear or branched alkanol (alcohol) with supply of CO and in the presence of a catalytic system composed of a palladium complex and at least one organic phosphorus ligand and in the presence of a hydrogen halide selected from HCl, HBr and HI.

10 Claims, No Drawings

PROCESS FOR DOUBLE CARBONYLATION OF ALLYL ETHERS TO CORRESPONDING DIESTERS

The invention relates to a process for doubly carbonylating allyl ethers to the corresponding diesters, wherein a linear or branched allyl ether is reacted with a linear or branched alkanol (alcohol) with supply of CO and in the presence of a catalytic system composed of a palladium complex and at least one organic phosphorus ligand and in the presence of a hydrogen halide selected from HCl, HBr and HI.

Allyl ethers are an important class of organic intermediates in the synthesis both of commodity chemicals and of fine chemicals. They are used for the synthesis of pharmaceutical intermediates, solvents, dyes, and functional materials. Among these applications, the carbonylating conversion of allyl ethers to industrial esters is one of the most common and most practised synthesis routes, particularly because of the enormous demand for these products in polymerization [Werle, P.; Morawietz, M., "*Alcohols, Polyhydric*" in *Ullmenn's Encyclopedia of Industrial Chemistry:* 2002, Wiley-VCH: Weinheim. 2002].

The standard methods to give diesters proceeding from allyl ethers require two steps (Scheme 1). The first step, the alkoxycarbonylation to give β,γ-unsaturated esters, was first described by Tsuji et al. in 1964 [Tsuji, J.; Kiji, J.; Imamura, S.; Morikawa, M., Organic Syntheses by Means of Noble Metal Compounds. VIII.1 Catalytic Carbonylation of Allylic Compounds with Palladium Chloride. *Journal of the American Chemical Society* 1964, 86 (20), 4350-4353]. In his studies, various allyl compounds including allyl ethers showed good reactivity and have been converted to the corresponding β,γ-unsaturated esters in the presence of palladium chloride as catalyst. In 1986, Hanes et al. developed a synthesis route for the alkoxycarbonylation of allyl ethers using less costly catalysts, for example nickel halides, cobalt halides and iron halides [Hanes, R. M.; Baugh, W. D., Carbonylation of allylic ethers to esters. U.S. Pat. No. 4,622,416 A: 1986]. Later, they also patented a method for preparation of esters from allyl ethers in the presence of group VIII transition metals as catalysts in the presence of halides [Hanes, R. M.; Kwiatek, J., Carbonylation of allylic ethers to esters. U.S. Pat. No. 5,004,568 A: 1991]. Recently, Belier et al. studied the mechanism of the alkoxycarbonylation of allyl alcohols and allenes, and showed that the allyl ethers formed are intermediates in these reactions [(a) Liu, J.; Liu, Q.; Franke, R.; Jackstell, R.; Beller, M., Ligand-Controlled Palladium-Catalyzed Alkoxycarbonylation of Allenes: Regioselective Synthesis of α,β- and β,γ-Unsaturated Esters (*Journal of the American Chemical Society* 2015, 137 (26), 8556-8563; (b) Liu, Q.; Wu, L.; Jiao, H.; Fang, X.; Jackstell, R.; Beller, M., Domino Catalysis: Palladium-Catalyzed Carbonylation of Allylic Alcohols to β,γ-Unsaturated Esters. *Angewandte Chemie International Edition* 2013, 52 (31), 8064-8068].

The second step is simply the alkoxycarbonylation of β,γ-unsaturated esters to give diesters (Scheme 1). This step is in principle the alkoxycarbonylation of alkenes, which are described in a number of publications and patents [Reppe, W.; Kröper, H., Carbonylierung II. Carbonsäuren und ihre Derivate aus olefinischen Verbindungen und Kohlenoxyd [Carbonylation II. Carboxylic Acids and Their Derivatives from Olefinic Compounds and Carbon Dioxide], *Justus Liebigs Annelen der Chemie* 1953, 582 (1), 38-71].

Scheme 1:

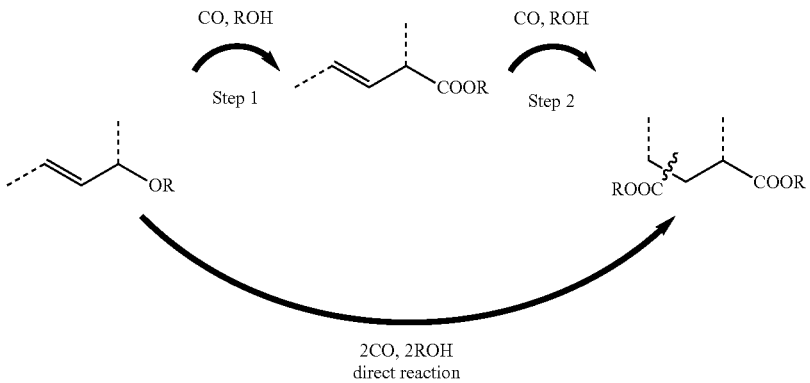

Even though all the abovementioned methods are well-developed and represent good reactivity for synthesis of diesters from allyl ethers, they require two reaction steps, which is a barrier to broad use in industrial applications.

It was therefore an object of the invention to look for effective processes for synthesis of diesters which avoid intermediate steps.

It is surprisingly possible to synthesize diesters in a one-step synthesis by a double carbonylation of allyl ethers. The object is achieved by a process according to Claim 1. The dependent claims constitute preferred process variants. The products prepared in accordance with the invention—the diesters—are preferably in the form of isomer mixtures.

The process for doubly carbonylating allyl ethers to diesters is characterized in that a linear or branched allyl ether is reacted with a linear or branched alkanol (alcohol) with supply of CO and in the presence of a catalytic system composed of a palladium complex and at least one organic phosphorus ligand and in the presence of a hydrogen halide selected from HCl, HBr and HI. Preferred hydrogen halides are HCl and HBr.

The allyl ethers used are preferably compounds of the general formula (1)

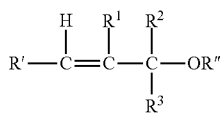

where $R^1$, $R^2$ and $R^3$ are independently hydrogen or a $C_1$ to $C_{10}$ alkyl radical and R' is hydrogen, or a saturated or unsaturated, branched or unbranched, aliphatic, cycloaliphatic or cycloaliphatic-aliphatic hydrocarbyl radical having up to 12 carbon atoms, in which C—C bonds may be interrupted by oxygen or the —O—CO— group, or a phenyl radical, where the phenyl radical may be substituted as follows: $C_1$- to $C_{10}$-alkyl or $C_1$- to $C_{10}$-alkoxy groups, R" is a saturated or unsaturated, branched or unbranched, aliphatic, cycloaliphatic, araliphatic or cycloaliphatic-aliphatic hydrocarbyl radical having up to 12 carbon atoms, in which C—C bonds may be interrupted by oxygen or the —O—CO— group.

R" is preferably a $C_1$ to $C_{12}$ alkyl or alkenyl radical, a $C_4$ to $C_{20}$-cycloalkyl radical, or a $C_7$- to $C_{11}$-aralkyl group.

Alkyl is preferably a branched or unbranched radical having 1 to 6 carbon atoms. Alkyl groups are, for example, methyl, ethyl, propyl, isopropyl, 1-butyl, 2-butyl, 1-pentyl, 1-hexyl.

The alcohols used in accordance with the Invention may be primary or secondary alcohols. It is possible to utilize aliphatic, cycloaliphatic, aromatic or else araliphatic alcohols, preference being given to employing aliphatic, cycloaliphatic and araliphatic alcohols. In general, alcohols ROH used in the process according to the invention are those in which the R radical is a $C_1$- to $C_{10}$-alkyl, a $C_4$- to $C_{20}$-cycloalkyl or a $C_7$- to $C_{11}$-aralkyl group.

Preference is given to reacting allyl ethers of the formula (1) with corresponding alcohols ROH in which R" corresponds to the R radical.

Phenyl for R' and R in ROH may optionally be substituted by substituents such as $C_1$- to $C_{10}$-alkoxy groups.

Preference is given to using alcohols ROH with unsubstituted R radicals. It is of course also possible to use alcohols having a relatively high number of carbon atoms. In particular, lower alkanols ($C_1$ to $C_6$) are used with preference.

Examples of aliphatic alcohols are, for example, methanol, ethanol, 1-propanol, 2-propanol, $C_4$ alcohols, e.g. 1-butanol, 2-butanol or isobutyl alcohol, $C_5$ alcohols, e.g. 1-pentanol, isoamyl alcohol or 2-pentanol, $C_6$ alcohols, e.g. 1-hexanol, 2-methyl-1-pentanol, 3-methyl-1-pentanol, 2,2-dimethyl-1-butanol, 2-ethyl-1-butanol, 4-ethyl-1-pentanol, 2-hexanol, 3-hexanol, 3-methyl-2-pentanol, 2,3-dimethyl-2-butanol, 2-methyl-3-pentanol, 3-methyl-3-pentanol, 4-methyl-2-pentanol, 2-methyl-2-pentanol, $C_7$ alcohols, e.g. n-heptyl alcohol, 2-methyl-1-hexyl alcohol, 3-methyl-1-hexyl alcohol, 4-methyl-1-hexyl alcohol, 5-methyl-1-hexyl alcohol, 2-ethyl-1-pentanol, 3-ethyl-1-pentanol, 2,2-dimethyl-1-pentanol, 3,3-dimethyl-1-pentanol, 4,4-dimethyl-1-pentanol, 2,3-dimethyl-1-pentanol, 2,4-dimethyl-1-pentanol, 3,4-dimethyl-1-pentanol, $C_8$ alcohols, e.g. 1-octanol, 2-methyl-1-heptanol, 3-methyl-1-heptanol, 4-methyl-1-heptanol, 5-methyl-1-heptanol, 2-octanol, 3-octanol, 4-octanol, 2-methyl-2-heptanol, 3-methyl-2-heptanol, 4-methyl-2-heptanol, 5-methyl-2-heptanol, 6-methyl-2-heptanol, 2-methyl-3-heptanol or 3-methyl-3-heptanol, and $C_9$ alcohols, e.g. 1-nonanol.

Examples of the alicyclic alcohols having 4 or more carbon atoms include alicyclic alcohols having 4 to 12 carbon atoms, for example cyclopentanol, cyclohexanol or cyclooctanol.

The $C_7$- to $C_{11}$-aralkyl group used is preferably the benzyl group.

In one variant of the process, the reaction is conducted in the liquid phase at a temperature of 70 to 250° C., preferably at 80 to 180° C., more preferably at temperatures of 100 to 150° C.

The reaction preferably takes place under a pressure of 2 to 100 bar. Preference is given to conducting the reaction under a pressure of 5 to 50 bar. In one process variant, as well as CO, nitrogen ($N_2$) can additionally be injected, preferably at a pressure p CO 40 bar+p $N_2$ 30 bar.

In one variant of the process, the palladium complex is formed in situ proceeding from a pre-complex, using, as palladium source, palladium-containing salts and complexes as precursor. The palladium compounds may be in different oxidation states, advantageously including the states of 0 to +11. Preferably, the palladium catalyst is selected from the group comprising Pd acetates, e.g. $Pd(OAc)_2$ and $Pd(TFA)_2$. Pd acetonates, e.g. $Pd(acac)_2$ and $Pd_2(dba)_3$, Pd halides and Pd halide complexes, e.g. $PdCl_2$, $Pd(MeCN)_2Cl_2$, $[PdCl(C_3H_5)]_2$ and Pd-halogen-1,5-cyclooctadienes, such as $Pd(cod)_2Cl_2$, Pd nitrates, Pd oxide.

The preferred phosphine ligands L have a mono- or bidentate structure. For example, the following ligands are used particularly advantageously in the process according to the invention:

L1—(9,9-dimethyl-9H-xanthene-4,5-diyl)bis(diphenylphosphine) (=Xantphos),
L2—(oxybis(2,1-phenylene))bis(di-tert-butylphosphine) (=DPEphos),
L3—1,2-bis((di-tert-butylphosphinyl)methyl)benzene,
L4—triphenylphosphine (=TPPO),
L5—di(1-adamantyl)-n-butylphosphine (=BuPAd?).

Xantphos is used with particular preference as ligand.

The palladium catalyst comprises the phosphine ligand preferably in a ratio of palladium to ligand in the range from 1:1 to 1:20, preferably in the range from 1:1 to 1:10, more preferably in the range from 1:1 to 1:3. The ratio of palladium to hydrogen halide is preferably in the range from 1:1 to 1:20. All ratios are molar ratios.

Effective amounts of catalyst in the process are preferably 0.01 to 12 mol % of palladium based on the alcohol, preference being given to using 0.05 mol % to 1.5 mol % of palladium, based on alcohol.

It is possible to use solvents for the process according to the invention. For example, polar inert organic solvents or/and water are used. For example, dipolar aprotic solvents, ethers, aliphatic ethers, amides, aromatic compounds, alcohols and esters, and mixtures thereof, are used. Particular preference is given to using aromatic compounds and aliphatic ethers such as toluene and diethyl ether.

Particular preference is given to using, in the process according to the invention, hydrogen chloride as hydrogen halide, preferably in an apolar organic solvent or solvent mixture. More particularly, the reaction is conducted in a mixture of HCl/diethyl ether and a further solvent, preferably toluene.

Surprisingly, it is possible by the process according to the invention to prepare the corresponding diesters, generally in the form of isomer mixtures, but also in the form of pure n compounds in good yields. The process is thus a diester synthesis of high atom and process economy. Surprisingly, yields of diesters up to 95% are attained.

The invention is elucidated in detail in examples which follow.

WORKING EXAMPLES

General Remarks:

All commercial reagents were ordered from Alfa Aesar, Aldrich, TCI or Strem. Unless stated otherwise, commercial reagents were used without purification. The allyl ether is distilled under reduced pressure prior to use. Toluene, DMF, THF, acetonitrile and methanol are used from the PS-MD-7 solvent purification system from "Innovative technology" using standard Schlenk techniques. Analytical data for the compounds known from the literature were in accordance with data reported. NMR spectra were recorded on the Bruker Avance 300 (300 MHz) NMR spectrometer. Multiplets were assigned as s (singlet), d (doublet), t (triplet), dd (doublet of doublets), m (multiplet) and br s (broad singlet). All measurements were conducted at room temperature, unless stated otherwise. Electron impact (EI) mass spectra were conducted on the AMD 402 mass spectrometer (70 eV). High-resolution mass spectra (HRMS) were recorded on the Agilent 6210 time-of-flight LC/MS (Agilent) with electrospray ionization (ESI). The data are reported as mass units per charge (m/z) and intensities of signals in brackets. The products were separated from the reaction mixture by column chromatography on silica gel 60, 0.063-0.2 mm, 70-230 mesh (Merck).

GC Analysis:

GC analysis was conducted by means of an Agilent GC 7890A gas chromatograph from Agilent Company with a 30 m HP-5 column ((polydimethylsiloxane with 5% phenyl groups, 30 m, 0.32 mm ID, 0.25 µm film thickness). Temperature program: 35° C., 10 min; 10° C./min to 285° C., 5 min; injection volume 1 µl with a split of 50:1.

List Of Abbreviations

BnOH: benzyl alcohol
CyOH: cyclohexanol
equiv.: equivalents
HCl: hydrogen chloride
THF: tetrahydrofuran
T: temperature
p: pressure
Xantphos: 4,5-bis(diphenylphosphinyl)-9,9-dimethylxanthene

Example 1

Reaction of Allyl Butyl Ether with Butanol Using Pd(OAc)$_2$ and Various Phosphine Ligands, and also Hydrogen Chloride (Table 1)

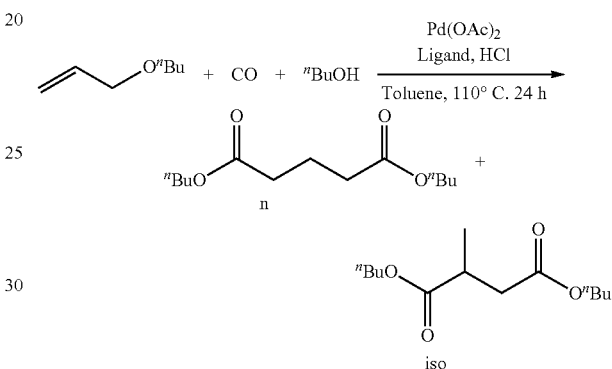

| Entry | Pd (mol %) | Ligand (mol %) | Solvent | Acid (mol %) | T (° C.) | p(bar) | Yield (n-/iso-) |
|---|---|---|---|---|---|---|---|
| 1 | Pd(OAc)$_2$(1.0) | L1 Xantphos (1.5 mol %) | toluene | HCl (2.0) | 110 | 40 bar CO | 90% (48:52) |
| 2 | Pd(OAc)$_2$(1.0) | L2 DPEphos (1.5 mol %) | toluene | HCl (2.0) | 110 | 40 bar CO | 2% (70:30) |
| 3 | Pd(OAc)$_2$(1.0) | L3 (1.5 mol %) | toluene | HCl (2.0) | 110 | 40 bar CO | 50% (36:64) |

-continued

| Entry | Pd (mol %) | Ligand (mol %) | Solvent | Acid (mol %) | T (° C.) | p(bar) | Yield (n-/iso-) |
|---|---|---|---|---|---|---|---|
| 4 | Pd(OAc)₂(1.0) | 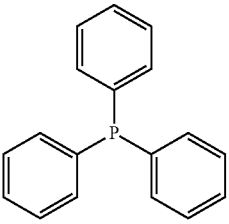<br>L4 (3.0 mol %) | toluene | HCl (2.0) | 110 | 40 bar CO | 4% (22:78) |
| 5 | Pd(OAc)₂(1.0) | 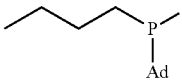<br>L5 (3.0 mol %) | toluene | HCl (2.0) | 110 | 40 bar CO | 4% (23:77) |

Example 1.1

Table 1, Entry 1

A 4 ml glass vial is charged with [Pd(acac)₂] (2.24 mg, 1 mol %), L1 (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (137 μl, 1.5 mmol), allyl butyl ether (145 μl, 1 mmol) and 1 M hydrochloric acid solution in diethyl ether (20 μl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 μl) is added as internal standard. The yield and selectivity are determined by means of GC analysis.

Example 1.2

Table 1, Entry 2

A 4 ml glass vial is charged with [Pd(acac)] (2.24 mg, 1 mol %), L2 (8.1 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (137 μl, 1.5 mmol), allyl butyl ether (145 μl, 1 mmol) and 1 M hydrochloric acid solution in diethyl ether (20 μl, 2 mol %) are then injected by means of syringes. This vial Is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 μl) is added as internal standard. The yield and selectivity are determined by means of GC analysis.

Example 1.3

Table 1, Entry 3

A 4 ml glass vial is charged with [Pd(acac)₂] (2.24 mg, 1 mol %), L3 (5.9 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (137 μl, 1.5 mmol), allyl butyl ether (145 μl, 1 mmol) and 1 M hydrochloric acid solution in diethyl ether (20 μl, 2 mol %) are then injected by means of syringes. This vial is then placed in a metal plate which is then transferred into a 300 ml steel autoclave from Parr Instruments under an argon atmosphere. After the autoclave has been purged three times with CO. CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 μl) is added as internal standard. The yield and selectivity are determined by means of GC analysis.

Example 1.4

Table 1, Entry 4

A 4 ml glass vial is charged with [Pd(acac)₂] (2.24 mg, 1 mol %), L4 (7.9 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (137 μl, 1.5 mmol), allyl butyl ether (145

μl, 1 mmol) and 1 M hydrochloric acid solution in diethyl ether (20 μl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 μl) is added as internal standard. The yield and selectivity are determined by means of GC analysis.

Example 1.5

Table 1, Entry 5

A 4 ml glass vial is charged with [Pd(acac)$_2$] (2.24 mg, 1 mol %), L5 (10.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (137 μl, 1.5 mmol), allyl butyl ether (145 μl, 1 mmol) and 1 M hydrochloric acid solution in diethyl ether (20 μl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 μl) is added as internal standard. The yield and selectivity are determined by means of GC analysis.

Example 2

Variation of the Amount of Acid (Table 2)

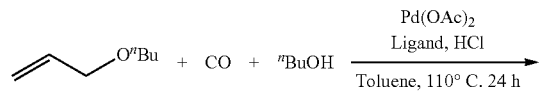

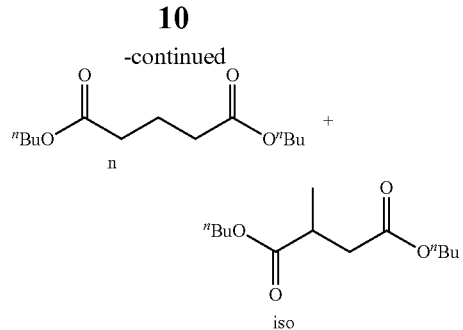

TABLE 2

| Entry | Pd (mol %) | Ligand (mol %) | Solvent | Acid (mol %) | T (° C.) | p (bar) | Yield (n-/iso-) |
|---|---|---|---|---|---|---|---|
| 1 | Pd(acac)$_2$ (1.0) | Xantphos (1.5) | toluene | HCl (1.0) | 110 | 40 | 25% (51:49) |
| 2 | Pd(acac)$_2$ (1.0) | Xantphos (1.5) | toluene | HCl (1.5) | 110 | 40 | 63% (49:51) |
| 3 | Pd(acac)$_2$ (1.0) | Xantphos (1.5) | toluene | HCl (2.0) | 110 | 40 | 78% (53:47) |
| 4 | Pd(acac)$_2$ (1.0) | Xantphos (1.5) | toluene | HCl (2.5) | 110 | 40 | 67% (48:52) |
| 5 | Pd(acac)$_2$ (1.0) | Xantphos (1.5) | toluene | HCl (3.0) | 110 | 40 | 22% (48:52) |
| 6 | Pd(acac)$_2$ (1.0) | Xantphos (1.5) | toluene | HCl (4.0) | 110 | 40 | 8% (46:54) |

Example 2.1

Table 2, Entry 1

A 4 ml glass vial is charged with [Pd(acac)$_2$] (3.07 mg, 1 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 μl, 2 mmol), allyl butyl ether (145 μl, 1 mmol) and 1 M hydrochloric acid solution in diethyl ether (10 μl, 1 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 μl) is added as internal standard. The yield and selectivity are determined by means of GC analysis.

Example 2.2

Table 2, Entry 2

A 4 ml glass vial is charged with [Pd(acac)$_2$] (3.07 mg, 1 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 μl, 2 mmol), allyl butyl ether (145 μl, 1 mmol) and 1 M hydrochloric acid solution in diethyl ether (15 µl, 1.5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 2.3

Table 2, Entry 3

A 4 ml glass vial is charged with [Pd(acac)$_2$] (3.07 mg, 1 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl butyl ether (145 µl, 1 mmol) and 1 M hydrochloric acid solution in diethyl ether (20 µl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 2.4

Table 2, Entry 4

A 4 ml glass vial is charged with [Pd(acac)$_2$] (3.07 mg, 1 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl butyl ether (145 µl, 1 mmol) and 1 M hydrochloric acid solution in diethyl ether (25 µl, 2.5 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 2.5

Table 2, Entry 5

A 4 ml glass vial is charged with [Pd(acac)$_2$] (3.07 mg, 1 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl butyl ether (145 µl, 1 mmol) and 1 M hydrochloric acid solution in diethyl ether (30 µl, 3 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 2.6

Table 2, Entry 6

A 4 ml glass vial is charged with [Pd(acac)$_2$] (3.07 mg, 1 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl butyl ether (145 µl, 1 mmol) and 1 M hydrochloric acid solution in diethyl ether (40 µl, 4 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 3

Variation of the Acids (Table 3)

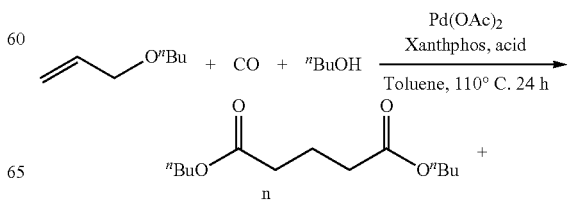

-continued

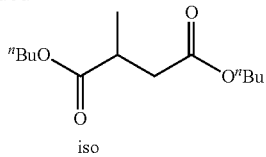

iso

TABLE 3

| Entry | Pd (mol %) | Ligand (mol %) | Solvent | Acid (mol %) | T (° C.) | p (bar) | Yield (n-/iso-) |
|---|---|---|---|---|---|---|---|
| 1 | Pd(OAc)$_2$ (1.0) | Xantphos (1.5) | toluene | HCl (2.0) | 110 | 40 | 90% (47:53) |
| 2 | Pd(OAc)$_2$ (1.0) | Xantphos (1.5) | toluene | H$_2$SO$_4$ (1.0) | 110 | 40 | 0 (—) |
| 3 | Pd(OAc)$_2$ (1.0) | Xantphos (1.5) | toluene | HOAc (2.0) | 110 | 40 | 0 (—) |
| 4 | Pd(OAc)$_2$ (1.0) | Xantphos (1.5) | toluene | CF$_3$COOH (2.0) | 110 | 40 | 0 (—) |
| 5 | Pd(OAc)$_2$ (1.0) | Xantphos (1.5) | toluene | CH$_3$SO$_3$H (2.0) | 110 | 40 | 0 (—) |
| 6 | Pd(OAc)$_2$ (1.0) | Xantphos (1.5) | toluene | CF$_3$SO$_3$H (2.0) | 110 | 40 | 0 (—) |
| 7 | Pd(OAc)$_2$ (1.0) | Xantphos (1.5) | toluene | PTSA•H$_2$O (2.0) | 110 | 40 | 0 (—) |
| 8 | Pd(OAc)$_2$ (1.0) | Xantphos (1.5) | toluene | — | 110 | 40 | 0 (—) |
| 9 | Pd(OAc)$_2$ (1.0) | Xantphos (1.5) | acetone | HCl (aq) (2.0) | 110 | 40 | 55 |
| 10 | Pd(OAc)$_2$ (1.0) | Xantphos (1.5) | acetone | HBr (aq) (2.0) | 110 | 40 | 11 |

Example 3.1

Table 3, Entry 1

A 4 ml glass vial is charged with [Pd(OAc)$_2$] (2.24 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl butyl ether (145 µl, 1 mmol) and 1 M hydrochloric acid solution in diethyl ether (20 µl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 3.2

Table 3, Entry 2

A 4 ml glass vial is charged with [Pd(OAc)$_2$] (2.24 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl butyl ether (145 µl, 1 mmol) and 0.5 M H$_2$SO$_4$ solution in diethyl ether (20 µl, 1.0 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 3.3

Table 3, Entry 3

A 4 ml glass vial is charged with [Pd(OAc)$_2$] (2.24 mg, 1.0 mol %). Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl butyl ether (145 µl, 1 mmol) and HOAc (1.1 µl, 2.0 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 3.4

Table 3, Entry 4

A 4 ml glass vial is charged with [Pd(OAc)$_2$] (2.24 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl butyl ether (145 µl, 1 mmol) and CF$_3$COOH (1.6 µl, 2.0 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 3.5

Table 3, Entry 5

A 4 ml glass vial is charged with [Pd(OAc)$_2$] (2.24 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl butyl ether (145 µl, 1 mmol) and CH$_3$SO$_3$H (1.3 µl, 2.0 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 3.6

Table 3, Entry 6

A 4 ml glass vial is charged with [Pd(OAc)$_2$] (2.24 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl butyl ether (145 µl, 1 mmol) and CF$_3$SO$_3$H (1.8 µl, 2.0 mol %) are then Injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110'C for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 3.7

Table 3, Entry 7

A 4 ml glass vial is charged with [Pd(OAc)$_2$] (2.24 mg, 1.0 mol %), Xantphos (L1) (8.7 mg, 1.5 mol %), PTSA.H$_2$O (3.8 mg, 2.0 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl butyl ether (145 µl, 1 mmol) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 3.8

Table 3, Entry 8

A 4 ml glass vial is charged with [Pd(OAc)$_2$] (2.24 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl butyl ether (145 µl, 1 mmol) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 3.9

Table 3, Entry 9

A 4 ml glass vial is charged with [Pd(OAc)$_2$] (2.24 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of acetone, n-butanol (137 µl, 1.5 mmol), allyl butyl ether (145 µl, 1 mmol) and 1 M HCl (aqueous solution) (20 µl, 2.0 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

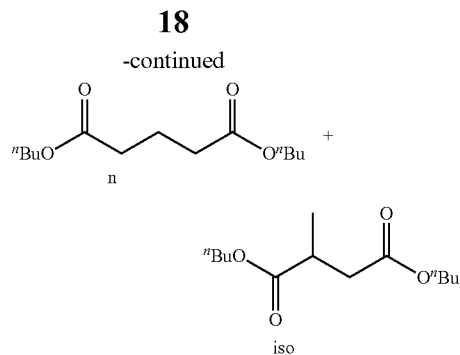

-continued

TABLE 4

| Entry | Pd (mol %) | Ligand (mol %) | nButanol (mol %) | Solvent | Acid (mol %) | T (° C.) | P (bar) | Yield (n-/iso-) |
|---|---|---|---|---|---|---|---|---|
| 1 | Pd(acac)$_2$ (1.0) | Xantphos (1.5) | 120 | toluene | HCl (2.0) | 110 | 40 | 79% (45:55) |
| 2 | Pd(acac)$_2$ (1.0) | Xantphos (1.5) | 150 | toluene | HCl (2.0) | 110 | 40 | 91% (46.54) |
| 3 | Pd(acac)$_2$ (1.0) | Xantphos (1.5) | 200 | toluene | HCl (2.0) | 110 | 40 | 85% (48:52) |
| 4 | Pd(acac)$_2$ (0.5) | Xantphos (0.75) | 200 | toluene | HCl (1.0) | 110 | 40 | 33% (50:50) |
| 5 | Pd(acac)$_2$ (0.25) | Xantphos (0.375) | 200 | toluene | HCl (0.5) | 110 | 40 | 6% (51:49) |

Example 3.10

Table 3, Entry 10

A 4 ml glass vial is charged with [Pd(OAc)$_2$] (2.24 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of acetone, n-butanol (137 µl, 1.5 mmol), allyl butyl ether (145 µl, 1 mmol) and 1 M HBr (aqueous solution) (20 µl, 2.0 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 4

Variation of the Amount of Palladium and of the Butanol (Table 4)

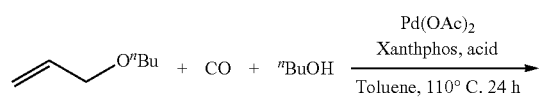

Example 4.1

Table 4, Entry 1

A 4 ml glass vial is charged with [Pd(acac)$_2$] (3.07 mg, 1 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (109 µl, 1.2 mmol), allyl butyl ether (145 µl, 1 mmol) and 1 M hydrochloric acid solution in diethyl ether (20 µl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 4.2

Table 4, Entry 2

A 4 ml glass vial is charged with [Pd(acac)$_2$] (3.07 mg, 1 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (137 µl, 1.5 mmol), allyl butyl ether (145 µl, 1 mmol) and 1 M hydrochloric acid solution in diethyl ether (20 µl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 4.3

Table 4, Entry 3

A 4 ml glass vial is charged with [Pd(acac)$_2$] (3.07 mg, 1 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl butyl ether (145 µl, 1 mmol) and 1 M hydrochloric acid solution in diethyl ether (20 µl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 4.4

Table 4, Entry 4

A 4 ml glass vial is charged with Xantphos (L1) (4.35 mg, 0.75 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. [Pd(acac)$_2$] (500 µl, 0.01 M in toluene, 1.53 mg, 0.5 mol %), toluene (1.5 ml), allyl butyl ether (145 µl, 1.0 mmol), n-butanol (182 µl, 2.0 mmol) and 1 M HCl-diethyl ether solution (10 µl, 1.0 mol %) are injected by means of a syringe. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 4.5

Table 4, Entry 5

A 4 ml glass vial is charged with Xantphos (L1) (2.18 mg, 0.375 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. [Pd(acac)$_2$] (250 µl, 0.01 M in toluene, 0.765 mg, 0.25 mol %), toluene (1.5 ml), allyl butyl ether (145 µl, 1.0 mmol), n-butanol (182 µl, 2.0 mmol) and 1 M HCl-diethyl ether solution (5 µl, 1.0 mol %) are injected by means of a syringe. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 5

Variation of the Amount of Xantphos (Table 5)

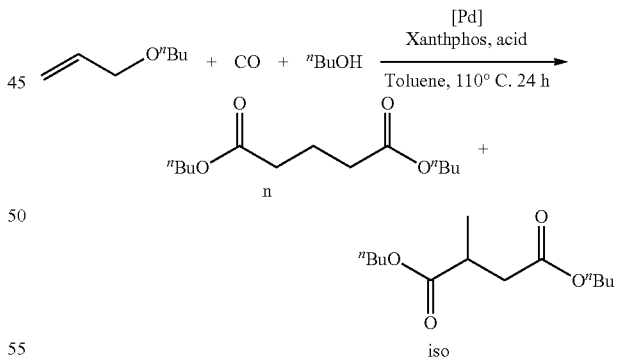

TABLE 5

| Entry | Pd (mol %) | Ligand (mol %) | Solvent | Acid (mol %) | T (° C.) | p (bar) | Yield (n-/iso-) |
|---|---|---|---|---|---|---|---|
| 1 | Pd(acac)$_2$ (1.0) | Xantphos (1.0) | toluene | HCl (2.0) | 110 | 40 | 7% (48:52) |
| 2 | Pd(acac)$_2$ (1.0) | Xantphos (1.5) | toluene | HCl (2.0) | 110 | 40 | 85% (47:53) |

TABLE 5-continued

| Entry | Pd (mol %) | Ligand (mol %) | Solvent | Acid (mol %) | T (° C.) | p (bar) | Yield (n-/iso-) |
|---|---|---|---|---|---|---|---|
| 3 | Pd(acac)$_2$ (1.0) | Xantphos (2.0) | toluene | HCl (2.0) | 110 | 40 | 62% (49:51) |

Example 5.1

Table 5, Entry 1

A 4 ml glass vial is charged with [Pd(acac)$_2$] (3.07 mg, 1 mol %), Xantphos (L1) (5.8 mg, 1.0 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl butyl ether (145 µl, 1 mmol) and 1 M hydrochloric acid solution in diethyl ether (20 µl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 5.2

Table 5, Entry 2

A 4 ml glass vial is charged with [Pd(acac)$_2$] (3.07 mg, 1 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl butyl ether (145 µl, 1 mmol) and 1 M hydrochloric acid solution in diethyl ether (20 µl, 2 mol %) are then injected by means of syringes. This vial is then placed in a metal plate which is then transferred into a 300 ml steel autoclave from Parr Instruments under an argon atmosphere. After the autoclave has been purged three times with CO, CO is Injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 5.3

Table 5, Entry 3

A 4 ml glass vial is charged with [Pd(acac)] (3.07 mg, 1 mol %), Xantphos (L1) (11.6 mg, 2 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl butyl ether (145 µl, 1 mmol) and 1 M hydrochloric acid solution in diethyl ether (20 µl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 6

Variation of the Palladium Precursor (Table 6)

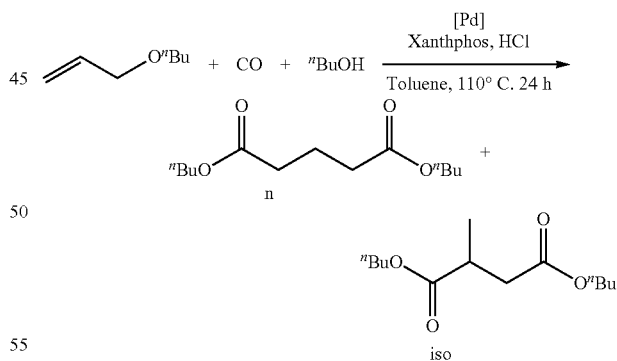

TABLE 6

| Entry | Pd (mol %) | Ligand (mol %) | nButanol (mol %) | Solvent | Acid (mol %) | T (° C.) | p (bar) | Yield (n-/iso-) |
|---|---|---|---|---|---|---|---|---|
| 1 | Pd(acac)$_2$ (1.0) | Xantphos (1.5) | 200 | toluene | HCl (2.0) | 110 | 40 | 85% (53:47) |
| 2 | Pd(OAc)$_2$ (1.0) | Xantphos (1.5) | 200 | toluene | HCl (2.0) | 110 | 40 | 89% (48:52) |

TABLE 6-continued

| Entry | Pd (mol %) | Ligand (mol %) | nButanol (mol %) | Solvent | Acid (mol %) | T (° C.) | p (bar) | Yield (n-/iso-) |
|---|---|---|---|---|---|---|---|---|
| 3 | PdCl$_2$ (1.0) | Xantphos (1.5) | 200 | toluene | HCl (2.0) | 110 | 40 | 90% (45:55) |
| 4 | Pd(MeCN)$_2$Cl$_2$ (1.0) | Xantphos (1.5) | 200 | toluene | HCl (2.0) | 110 | 40 | 90% (44:56) |
| 5 | Pd(cod)$_2$Cl$_2$ (1.0) | Xantphos (1.5) | 200 | toluene | HCl (2.0) | 110 | 40 | 85% (45:55) |
| 6 | [PdCl(C$_3$H$_5$)]$_2$ (1.0) | Xantphos (1.5) | 200 | toluene | HCl (2.0) | 110 | 40 | 87% (48:52) |
| 7 | Pd$_2$(dba)$_3$ (1.0) | Xantphos (1.5) | 200 | toluene | HCl (2.0) | 110 | 40 | 82% (49:51) |
| 8 | Pd(TFA)$_2$ | Xantphos (1.5) | 200 | toluene | HCl (2.0) | 110 | 40 | 93% (49:51) |
| 9 | Pd(acac)$_2$ (1.0) | Xantphos (1.5) | 150 | toluene | HCl (2.0) | 110 | 40 bar CO + 30 bar N$_2$ | 87% (45:55) |
| 10 | Pd(OAc)$_2$ (1.0) | Xantphos (1.5) | 150 | toluene | HCl (2.0) | 110 | 40 bar CO + 30 bar N$_2$ | 92% (45:55) |
| 11 | Pd(TFA)$_2$ (1.0) | Xantphos (1.5) | 150 | toluene | HCl (2.0) | 110 | 40 bar CO + 30 bar N$_2$ | 94% (47:53) |
| 12 | PdO (1.0) | Xantphos (1.5) | 200 | toluene | HCl (2.0) | 110 | 40 bar CO | 73% (48:52) |
| 13 | Pd(NO$_3$)$_2$ 2H$_2$O (1.0) | Xantphos (1.5) | 200 | toluene | HCl (2.0) | 110 | 40 bar CO | 74% (49:51) |

Example 6.1

Table 6, Entry 1

A 4 ml glass vial is charged with [Pd(acac)$_2$] (3.07 mg, 1 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl butyl ether (145 µl, 1 mmol) and 1 M hydrochloric acid solution in diethyl ether (20 µl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 6.2

Table 6, Entry 2

A 4 ml glass vial is charged with [Pd(OAc)$_2$] (2.24 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl butyl ether (145 µl, 1 mmol) and 1 M hydrochloric acid solution in diethyl ether (20 µl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 6.3

Table 6, Entry 3

A 4 ml glass vial is charged with [PdCl$_2$] (1.76 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl butyl ether (145 µl, 1 mmol) and 1 M hydrochloric acid solution in diethyl ether (20 µl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 6.4

Table 6, Entry 4

A 4 ml glass vial is charged with [Pd(MeCN)$_2$Cl$_2$] (2.58 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl butyl ether (145 µl, 1 mmol) and 1 M hydrochloric acid solution in diethyl ether (20 µl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 6.5

Table 6, Entry 5

A 4 ml glass vial is charged with [Pd(cod)$_2$Cl$_2$] (2.85 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl butyl ether (145 µl, 1 mmol) and 1 M hydrochloric acid solution in diethyl ether (20 µl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 6.6

Table 6, Entry 6

A 4 ml glass vial is charged with [PdCl(C$_3$H$_5$)]$_2$ (1.83 mg, 0.5 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl butyl ether (145 µl, 1 mmol) and 1 M hydrochloric acid solution in diethyl ether (20 µl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 6.7

Table 6, Entry 7

A 4 ml glass vial is charged with [Pd$_2$(dba)$_3$] (4.58 mg, 0.5 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl butyl ether (145 µl, 1 mmol) and 1 M hydrochloric acid solution in diethyl ether (20 µl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 6.8

Table 6, Entry 8

A 4 ml glass vial is charged with [Pd(TFA)$_2$] (3.32 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula. 2 ml of toluene, n-butanol (182 µl, 2 mmol), allyl butyl ether (145 µl, 1 mmol) and 1 M hydrochloric acid solution in diethyl ether (20 µl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 6.9

Table 6, Entry 9

A 4 ml glass vial is charged with [Pd(acac)$_2$] (3.07 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (136 µl, 1.5 mmol), allyl butyl ether (145 µl, 1 mmol) and 1 M hydrochloric acid solution in diethyl ether (20 µl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar and nitrogen (5.0 purity) to 30 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 6.10

Table 6, Entry 10

A 4 ml glass vial is charged with [Pd(OAc)$_2$] (2.24 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (136 µl, 1.5 mmol), allyl butyl ether (145 µl, 1 mmol) and 1 M hydrochloric acid solution in diethyl ether (20 µl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar and nitrogen (5.0 purity) to 30 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 6.11

Table 6, Entry 11

A 4 ml glass vial is charged with [Pd(TFA)$_2$] (3.32 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (136 µl, 1.5 mmol), allyl butyl ether (145 µl, 1 mmol) and 1 M hydrochloric acid solution in diethyl ether (20 µl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar and nitrogen (5.0 purity) to 30 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 6.12

Table 6, Entry 12

A 4 ml glass vial is charged with PdO (1.2 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl butyl ether (145 µl, 1 mmol) and 1 M hydrochloric acid solution in diethyl ether (20 µl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 6.13

Table 6, Entry 13

A 4 ml glass vial is charged with [Pd(NO$_3$)$_2$.2H$_2$O] (2.65 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl butyl ether (145 µl, 1 mmol) and 1 M hydrochloric acid solution in diethyl ether (20 µl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 7

Variation of the Solvent, Table 7

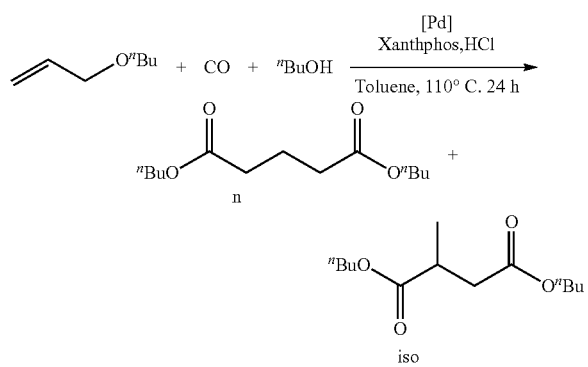

TABLE 7

| Entry | Pd (mol %) | Ligand (mol %) | Solvent | Acid (mol %) | Temp (° C.) | pbar | Yield (n-/iso-) |
|---|---|---|---|---|---|---|---|
| 1 | Pd(acac)$_2$ (1.0) | Xantphos (1.5) | toluene | HCl (2.0) | 110 | 40 | 85% (47:53) |
| 2 | Pd(acac)$_2$ (1.0) | Xantphos (1.5) | THF | HCl (2.0) | 110 | 40 | 27% (45:55) |
| 3 | Pd(acac)$_2$ (1.0) | Xantphos (1.5) | MeCN | HCl (2.0) | 110 | 40 | 6% (66:34) |
| 4 | Pd(acac)$_2$ (1.0) | Xantphos (1.5) | heptane | HCl (2.0) | 110 | 40 | 18% (57:43) |
| 5 | Pd(acac)$_2$ (1.0) | Xantphos (1.5) | acetone | HCl (2.0) | 110 | 40 | 60% (54:46) |
| 6 | Pd(acac)$_2$ (1.0) | Xantphos (1.5) | dioxane | HCl (2.0) | 110 | 40 | 20% (48:52) |
| 7 | Pd(acac)$_2$ (1.0) | Xantphos (1.5) | n-butanol | HCl (2.0) | 110 | 40 | 6% (76:24) |

Table 7, Entry 1

A 4 ml glass vial is charged with [Pd(acac)$_2$] (3.07 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butanol (182 µl, 2 mmol), allyl butyl ether (145 µl, 1 mmol) and 1 M hydrochloric acid solution in diethyl ether (20 µl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 7.2

Table 7, Entry 2

A 4 ml glass vial is charged with [Pd(acac)$_2$] (3.07 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of THF, n-butanol (182 µl, 2 mmol), allyl butyl ether (145 µl, 1 mmol) and 1 M hydrochloric acid solution in diethyl ether (20 µl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 7.3

Table 7, Entry 3

A 4 ml glass vial is charged with [Pd(acac)$_2$] (3.07 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of MeCN, n-butanol (182 µl, 2 mmol), allyl butyl ether (145 µl, 1 mmol) and 1 M hydrochloric acid solution in diethyl ether (20 µl, 2 mol %) are then injected by means of syringes. This vial is then placed in a metal plate which is then transferred into a 300 ml steel autoclave from Parr Instruments under an argon atmosphere. After the autoclave has been purged three times with CO. CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently,

Example 7.4

Table 7, Entry 4

A 4 ml glass vial is charged with [Pd(acac)₂] (3.07 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of heptane, n-butanol (182 μl, 2 mmol), allyl butyl ether (145 μl, 1 mmol) and 1 M hydrochloric acid solution in diethyl ether (20 μl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 μl) is added as Internal standard. The yield and selectivity are determined by means of GC analysis.

Example 7.5

Table 7, Entry 5

A 4 ml glass vial is charged with [Pd(acac)₂] (3.07 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of acetone, n-butanol (182 μl, 2 mmol), allyl butyl ether (145 μl, 1 mmol) and 1 M hydrochloric acid solution in diethyl ether (20 μl, 2 mol %) are then Injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 μl) is added as internal standard. The yield and selectivity are determined by means of GC analysis.

Example 7.6

Table 7, Entry 6

A 4 ml glass vial is charged with [Pd(acac)₂] (3.07 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of dioxane, n-butanol (182 μl, 2 mmol), allyl butyl ether (145 μl, 1 mmol) and 1 M hydrochloric acid solution in diethyl ether (20 μl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 μl) is added as internal standard. The yield and selectivity are determined by means of GC analysis.

Example 7.7

Table 7, Entry 7

A 4 ml glass vial is charged with [Pd(acac)₂] (3.07 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of n-butanol, n-butanol (182 μl, 2 mmol), allyl butyl ether (145 μl, 1 mmol) and 1 M hydrochloric acid solution in diethyl ether (20 μl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 μl) is added as internal standard. The yield and selectivity are determined by means of GC analysis.

Example 8

Variation of Substrate (Table 8)

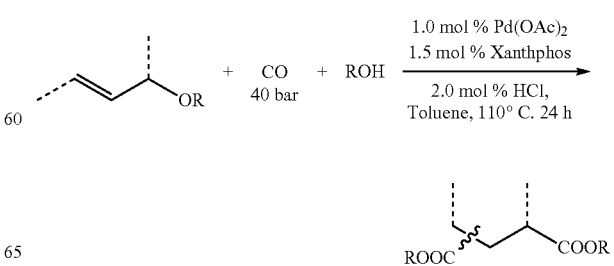

TABLE 8

| Entry | Substrate | Alcohol | Main products | Yield (n-/iso-) |
|---|---|---|---|---|
| 1 | allyl-OMe | MeOH (1.5 equiv.) | MeOOC~~~COOMe; MeOOC-CH(Me)-COOMe | 81% (50:50) |
| 2 | allyl-OEt | EtOH (1.5 equiv.) | EtOOC~~~COOEt; EtOOC-CH(Me)-COOEt | 83% (46:54) |
| 3 | allyl-O$^n$Bu | $^n$BuOH (1.5 equiv.) | $^n$BuOOC~~~COO$^n$Bu; $^n$BuOOC-CH(Me)-COO$^n$Bu | 90% (48:52) |
| 4 | allyl-OBn | BnOH (1.5 equiv.) | BnOOC~~~COOBn; BnOOC-CH(Me)-COOBn | 70% (70%[b]) (48:52) |
| 5 | allyl-O-Cy | CyOH (1.5 equiv.) | CyOOC~~~COOCy; CyOOC-CH(Me)-COOCy | 61% (53:47) |
| 6 | allyl-O-allyl | $^n$BuOH (6.0 equiv.) | $^n$BuOOC~~~COO$^n$Bu; $^n$BuOOC-CH(Me)-COO$^n$Bu | 93% (54:46) |
| 7 | CH2=CH-CH(Me)OBn | BnOH (1.5 equiv.) | BnOOC~~~~COOBn; BnOOC-CH(Me)-CH2-COOBn; BnOOC-CH(Et)-COOBn | 61% (6:94) |
| 8 | MeCH=CH-CH2-OBn | BnOH (1.5 equiv.) | BnOOC~~~~COOBn; BnOOC-CH(Me)-CH2-COOBn; BnOOC-CH(Et)-COOBn | 44% (7:93) |

TABLE 8-continued

| Entry | Substrate | Alcohol | Main products | Yield (n-/iso-) |
|---|---|---|---|---|
| 9[a] | Ph⌒⌒OMe | MeOH (1.5 equiv.) | Ph on MeOOC⌒⌒COOMe; and MeOOC-CH(CH2Ph)-CH2-COOMe | 35%[b] (69:31) |

[a] 4.0 mol % HCl, 48 h
[b] Isolated yield

Example 8.1

Table 8, Entry 1

A 4 ml glass vial is charged with [Pd(OAc)$_2$] (2.24 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, methyl allyl ether (72 mg, 1.0 mmol), methanol (48 mg, 1.5 mmol) and 1 M hydrochloric acid solution in diethyl ether (20 μl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 μl) is added as internal standard. The yield and selectivity are determined by means of GC analysis.

Example 8.2

Table 8, Entry 2

A 4 ml glass vial is charged with [Pd(OAc)$_2$] (2.24 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, ethyl allyl ether (86 mg, 2 mmol), ethanol (69 mg, 1.5 mmol) and 1 M hydrochloric acid solution in diethyl ether (20 μl, 1.0 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 μl) is added as internal standard. The yield and selectivity are determined by means of GC analysis.

Example 8.3

Table 8, Entry 3

A 4 ml glass vial is charged with [Pd(OAc)$_2$] (2.24 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, n-butyl allyl ether (114 mg, 1.0 mmol), n-butanol (111 mg, 1.5 mmol) and 1 M hydrochloric acid solution in diethyl ether (20 μl, 2 mol %) are then injected by means of syringes. This vial is then placed in a metal plate which is then transferred into a 300 ml steel autoclave from Parr Instruments under an argon atmosphere. After the autoclave has been purged three times with CO, CO is Injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 μl) is added as internal standard. The yield and selectivity are determined by means of GC analysis.

Example 8.4

Table 8, Entry 4

A 4 ml glass vial is charged with [Pd(OAc)$_2$] (2.24 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, benzyl allyl ether (148 mg, 1.0 mmol), BnOH (162 mg, 1.5 mmol) and 1 M hydrochloric acid solution in diethyl ether (20 μl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 μl) is added as internal standard. The yield and selectivity are determined by means of GC analysis.

Example 8.5

Table 8, Entry 5

A 4 ml glass vial is charged with [Pd(OAc)$_2$] (2.24 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, cyclohexyl allyl ether (140 mg, 1.0 mmol), CyOH (150 mg, 1.5 mmol) and 1 M hydrochloric acid solution in diethyl ether (20 µl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 8.6

Table 8, Entry 6

A 4 ml glass vial is charged with [Pd(OAc)$_2$] (2.24 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, diallyl ether (98 mg, 1.0 mmol), n-butanol (444 mg, 6.0 mmol) and 1 M hydrochloric acid solution in diethyl ether (20 µl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 8.7

Table 8, Entry 7

A 4 ml glass vial is charged with [Pd(OAc)$_2$] (2.24 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, ((but-3-en-2-yloxy)methyl)benzene (162 mg, 1.0 mmol), BnOH (162 mg, 1.5 mmol) and 1 M hydrochloric acid solution in diethyl ether (20 µl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 8.8

Table 8, Entry 8

A 4 ml glass vial is charged with [Pd(OAc)$_2$] (2.24 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, ((but-2-en-1-yloxy)methyl)benzene (162 mg, 1.0 mmol), BnOH (162 mg, 1.5 mmol) and 1 M hydrochloric acid solution in diethyl ether (20 µl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 8.9

Table 8 Entry 9

A 4 ml glass vial is charged with [Pd(OAc)$_2$] (2.24 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of toluene, (3-methoxyprop-1-en-1-yl)benzene (148 mg, 1.0 mmol), MeOH (48 mg, 1.5 mmol) and 2 M HCl solution in diethyl ether (20 µl, 4.0 mol %) are then injected by means of syringes. This vial is then placed in a metal plate which is then transferred into a 300 ml steel autoclave from Parr Instruments under an argon atmosphere. After the autoclave has been purged three times with CO, CO Is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 µl) is added as internal standard. The yield and selectivity are determined by means of GC analysis.

Example 9

Variation of Temperature (Table 9)

| Entry | Pd (mol %) | Ligand (mol %) | Solvent | Acid (mol %) | Temp (° C.) | p(bar) | Yield (n-/iso-) |
|---|---|---|---|---|---|---|---|
| 1 | Pd(acac)$_2$ (1.0) | Xantphos (1.5) | toluene | HCl (2.0) | 100 | 40 | 64% (48:52) |
| 2 | Pd(acac)$_2$ (1.0) | Xantphos (1.5) | toluene | HCl (2.0) | 110 | 40 | 85% (53:47) |
| 3 | Pd(acac)$_2$ (1.0) | Xantphos (1.5) | toluene | HCl (2.0) | 120 | 40 | 77% (48:52) |
| 4 | Pd(acac)$_2$ (1.0) | Xantphos (1.5) | toluene | HCl (2.0) | 140 | 40 | 75% (48:52) |

Example 9.1

Table 9, Entry 1

A 4 ml glass vial is charged with [Pd(acac)$_2$] (3.07 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of propylene carbonate, n-butanol (182 μl, 2 mmol), allyl butyl ether (145 μl, 1 mmol) and 1 M hydrochloric acid solution in diethyl ether (20 μl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 100° C. for 24 hours. After the end of the reaction, the autoclave is cooled down and the pressure is released gradually. The autoclave is purged three times with nitrogen. Subsequently, dodecane (100 μl) is added as internal standard. The yield and selectivity are determined by means of GC analysis.

Example 9.2

Table 9, Entry 2

A 4 ml glass vial is charged with [Pd(acac)$_2$] (3.07 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of propylene carbonate, n-butanol (182 μl, 2 mmol), allyl butyl ether (145 μl, 1 mmol) and 1 M hydrochloric acid solution in diethyl ether (20 μl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 110° C. for 24 hours. After the end of the reaction, the autoclave is cooled down and the pressure is released gradually. The autoclave is purged three times with nitrogen. Subsequently, dodecane (100 μl) is added as internal standard. The yield and selectivity are determined by means of GC analysis.

Example 9.3

Table 9, Entry 3

A 4 ml glass vial is charged with [Pd(acac)$_2$] (3.07 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of propylene carbonate, n-butanol (182 μl, 2 mmol), allyl butyl ether (145 μl, 1 mmol) and 1 M hydrochloric acid solution in diethyl ether (20 μl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 120° C. for 24 hours. After the end of the reaction, the autoclave is cooled down and the pressure is released gradually. The autoclave is purged three times with nitrogen. Subsequently, dodecane (100 μl) is added as internal standard. The yield and selectivity are determined by means of GC analysis.

Example 9.4

Table 9, Entry 4

A 4 ml glass vial is charged with [Pd(acac)$_2$] (3.07 mg, 1.0 mol %), Xantphos (L1) (8.7 mg, 1.5 mol %) and a magnetic stirrer. This vial is closed with a phenolic resin cap consisting of a septum made from Teflon-coated styrene-butadiene rubber. This septum is pierced with a cannula, and the atmosphere in the vial is replaced by an argon atmosphere through this cannula by three cycles of application of reduced pressure and purging with argon. Through this cannula, 2 ml of propylene carbonate, n-butanol (182 μl, 2 mmol), allyl butyl ether (145 μl, 1 mmol) and 1 M hydrochloric acid solution in diethyl ether (20 μl, 2 mol %) are then injected by means of syringes. This vial is then placed in a metal plate which is then transferred into a 300 ml steel autoclave from Parr Instruments under an argon atmosphere. After the autoclave has been purged three times with CO, CO is injected to 40 bar at room temperature. The reaction is conducted while stirring with a magnetic stirrer at 140'C for 24 hours. After the end of the reaction, the autoclave is cooled down and the pressure is released gradually. The autoclave is purged three times with nitrogen. Subsequently, dodecane (100 μl) is added as internal standard. The yield and selectivity are determined by means of GC analysis.

The invention claimed is:

1. Process for doubly carbonylating allyl ethers to diesters, comprising: reacting, in a single step, a linear or branched allyl ether with a linear or branched alkanol with supply of CO and in the presence of a catalytic system composed of a palladium complex and at least one organic phosphorus ligand and in the presence of a hydrogen halide selected from HCl, HBr and HI,
wherein both the allyl portion and the ether portion of the allyl ether are reacted with the CO.

2. Process according to claim 1, characterized in that the allyl ethers are compounds of the general formula (1):

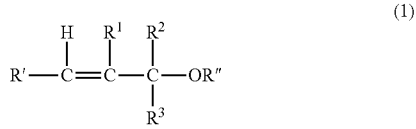
(1)

where $R^1$, $R^2$ and $R^3$ are independently hydrogen or a $C_1$ to $C_{10}$ alkyl radical and R' is hydrogen, or a saturated or unsaturated, branched or unbranched, aliphatic, cycloaliphatic or cycloaliphatic-aliphatic hydrocarbyl radical having up to 12 carbon atoms, in which C—C bonds may be interrupted by oxygen or the —O—CO— group, or a phenyl radical, where the phenyl radical may be substituted as follows: $C_1$- to $C_{10}$-alkyl or $C_1$- to $C_{10}$-alkoxy groups, R" is a saturated or unsaturated, branched or unbranched, aliphatic, cycloaliphatic, araliphatic or cycloaliphatic-aliphatic hydrocarbyl radical having up to 12 carbon atoms, in which C—C bonds may be interrupted by oxygen or the —O—CO— group.

3. Process according to claim 1, characterized in that the alkanols are compounds of the general formula ROH where R is a $C_1$- to $C_{10}$-alkyl, a $C_4$- to $C_{20}$-cycloalkyl or a $C_7$- to $C_{11}$-aralkyl group.

4. Process according to claim 1, characterized in that the reaction is conducted in the liquid phase at a temperature of 70 to 250° C.

5. Process according to claim 1, characterized in that reaction is conducted under a pressure of 2 to 100 bar.

6. Process according to claim 1, characterized in that the palladium complex is formed in situ proceeding from a pre-complex, using, as palladium source, palladium-containing salts and complexes as precursor.

7. Process according to claim 6, characterized in that the palladium complex is selected from the group comprising Pd acetates, Pd acetonates, Pd halides and Pd halide complexes, and also Pd-halogen-1,5-cyclooctadienes, Pd nitrates and Pd oxide.

8. Process according to claim 1, characterized in that the phosphine ligands have a mono- or bidentate structure, preferably selected from the group comprising
L1—(9,9-dimethyl-9H-xanthene-4,5-diyl)bis(diphenylphosphine),
L2—(oxybis(2,1-phenylene))bis(di-tert-butylphosphine),
L3—1,2-bis((di-tert-butylphosphinyl)methyl)benzene,
L4—triphenylphosphine,
L5—di(1-adamantyl)-n-butylphosphine.

9. Process according to claim 1, characterized in that the hydrogen halide used is hydrogen chloride.

10. Process according to claim 1, characterized in that the ratio of palladium to hydrogen halide is in the range from 1:1 to 1:20.

* * * * *